United States Patent [19]
Narayan et al.

[11] Patent Number: 5,176,688
[45] Date of Patent: Jan. 5, 1993

[54] STONE EXTRACTOR AND METHOD

[76] Inventors: Perinchery Narayan, 325 San Leandro Way, San Francisco, Calif. 94127; Maxim D. Persidsky, 35 Temescal Ter., San Francisco, Calif. 94118

[21] Appl. No.: 731,820

[22] Filed: Jul. 17, 1991

[51] Int. Cl.⁵ .............................................. A61B 17/00
[52] U.S. Cl. ......................................... 606/128; 606/1; 606/127; 606/170; 606/171; 606/185
[58] Field of Search ............... 606/127, 128, 167, 181, 606/182, 184, 185, 159, 170, 171; 128/7

[56] References Cited

U.S. PATENT DOCUMENTS

| | | | |
|---|---|---|---|
| 2,227,727 | 1/1941 | Leggiadro | 606/128 |
| 2,943,626 | 7/1960 | Dormia | 606/127 |
| 3,008,467 | 11/1961 | Morris | 606/127 |
| 4,046,149 | 9/1977 | Komiya | 606/127 |
| 4,198,960 | 4/1980 | Utsigi | 606/127 |
| 4,203,429 | 5/1980 | Vasilevsky et al. | 606/128 |
| 4,227,532 | 10/1980 | Bluhm et al. | 606/128 |
| 4,557,255 | 12/1985 | Goodman | 128/7 |
| 4,611,594 | 9/1986 | Grayback et al. | 606/127 |
| 4,936,845 | 6/1990 | Stevens | 606/159 |
| 5,036,860 | 8/1991 | Leigh et al. | 606/171 |

FOREIGN PATENT DOCUMENTS 0003374 12/1833 France ........................... 606/127

Primary Examiner—Stephen C. Pellegrino
Assistant Examiner—Glenn Dawson
Attorney, Agent, or Firm—Flehr, Hohbach, Test, Albritton & Herbert

[57] ABSTRACT

Instrument and method for removing stones (calculi) from the kidneys, the bladder and other parts of the body. A stone is captured in a basket at the distal end of an elongated tubular member and broken into pieces while it is held by the basket. The stone is broken up by a hammering action provided by a reciprocating shaft which extends through the tubular member into the basket and is driven toward the stone by a spring. The stone is removed from the body by withdrawing the tubular member from the body with the pieces of the stone in the basket. Since the tip of the shaft impacts upon the stone inside the basket, the instrument is safe in that the reciprocate tip cannot strike the tissue outside the basket.

13 Claims, 2 Drawing Sheets

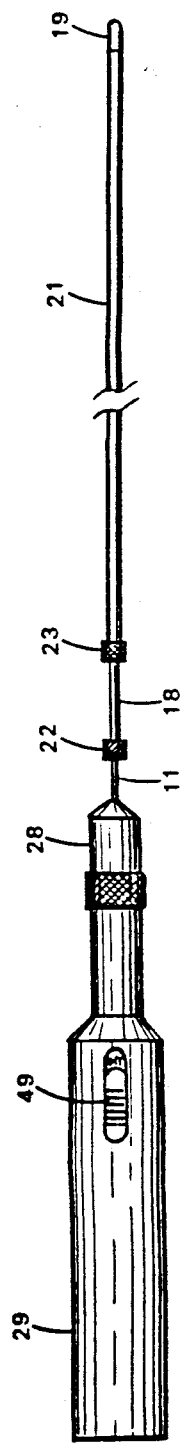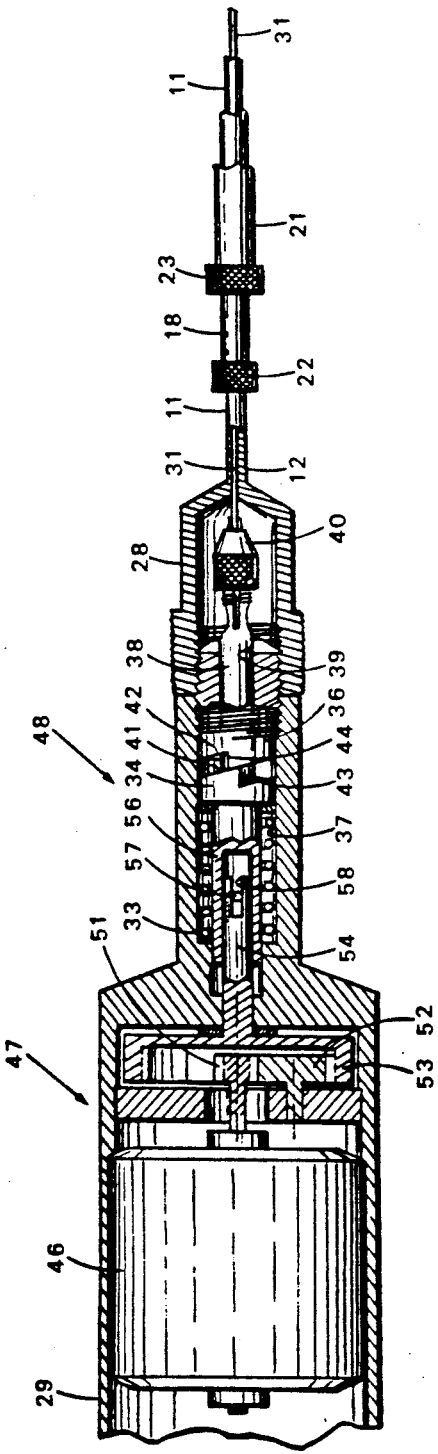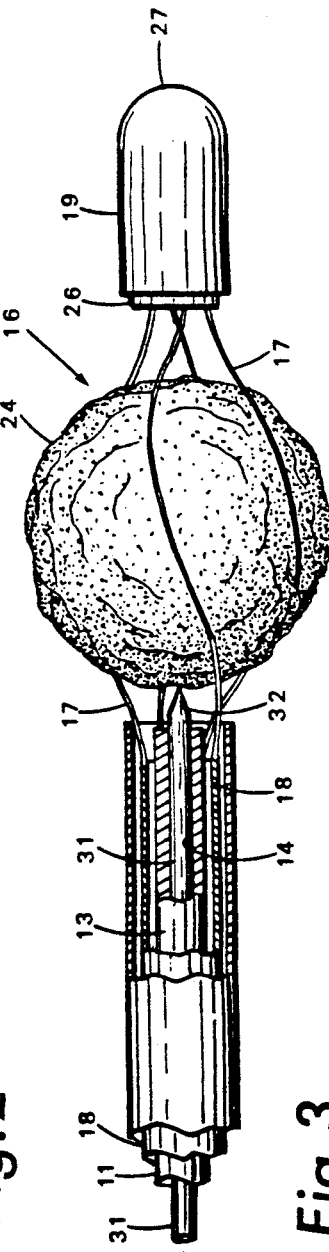

STONE EXTRACTOR AND METHOD

This invention pertains generally to the removal of stones (calculi) from the kidneys, the bladder and other parts of the body and, more particularly, to a stone extractor and method of the type in which the stones are broken into pieces for easier removal.

Several techniques are presently employed in clinical practice for breaking stones into pieces for removal from the body, including extra-corporeally applied shock waves, electro-hydraulic techniques, ultrasonic techniques and laser techniques. All of these techniques, however, have certain limitations and disadvantages such as high cost and risk to the patient.

Of the current techniques, extra-corporeal shock waves are probably the most popular and involve the lowest degree of risk. However, this technique requires relatively expensive equipment, and the shock waves are not very effective in breaking up harder stones. Ultrasound is likewise relatively ineffective with harder stones.

The electro-hydraulic technique is effective in breaking up harder stones, but presents a greater degree of risk than some of the other techniques since fragments produced by the explosive break up of stones can embed in the surrounding tissue and lead to the development of further stones.

Laser techniques are also effective in breaking up harder stones, but they require relatively expensive equipment, and the safety of these techniques has not been fully established.

All of these techniques have additional disadvantages in that they may require prolonged operating times and/or hospitalization of the patient.

Heretofore, there have also been some attempts to break up stones with mechanical devices which are introduced into the body percutaneously or through hollow organs. Some of these devices have rotating heads for hammering at and breaking up the stones, and examples of such devices are found in U.S. Pat. Nos. 4,664,112, 4,681,106 and 4,811,735. A device in which a reciprocating rod is driven by a crank for jabbing at a stone is found in U.S. Pat. No. 2,227,727. The crank produces a sinusoidal motion rather than an effective hammering action, and there is a danger of injury to the body tissue by the reciprocating rod.

It is in general an object of the invention to provide a new and improved instrument and method for removing stones from the body.

Another object of the invention is to provide an instrument and method of the above character which overcome the limitations and disadvantages of techniques heretofore employed for removing such stones.

Another object of the invention is to provide an instrument and method of the above character which can be employed effectively with stones of different sides and in different parts of the body.

These and other objects are achieved in accordance with the invention by providing a stone extractor and method in which a stone is captured in a basket at the distal end of an elongated tubular member and broken into pieces while it is held by the basket. The stone is broken up by a reciprocating shaft which extends through the tubular member into the basket and is driven toward the stone by a spring to provide an effective hammering action without injuring the surrounding tissue. The stone is removed from the body by withdrawing the tubular member from the body with the pieces of the stone in the basket.

FIG. 1 is an elevational view of one embodiment of a stone extractor incorporating the invention.

FIG. 2 is an enlarged fragmentary elevational view, partly broken away, of the proximal end portion of the embodiment of FIG. 1.

FIG. 3 is an enlarged fragmentary elevational view, partly broken away, of the distal end portion of the embodiment of FIG. 1, with the basket shown in an open position holding a stone.

Figure 4:
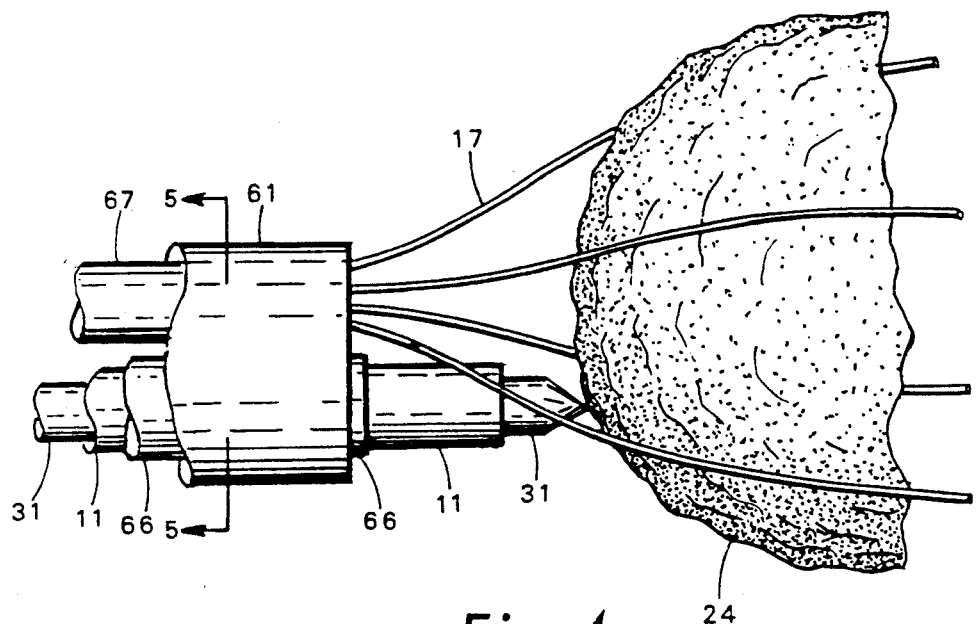
FIG. 4 is an enlarged fragmentary elevational view, partly broken away, of another embodiment of a stone extractor incorporating the invention.

As illustrated in the drawings, the stone extractor includes an elongated, catheter-like tubular member 11 which has a proximal end 12, a distal end 13 and an axially extending opening or bore 14. This member is fabricated of a relatively stiff yet somewhat pliant material such as nylon or polyester which permits the device to be introduced into the body along a tortuous path.

A basket 16 is provided at the distal end of the tubular member for capturing and holding stones for removal from the body. In the embodiment illustrated, the basket is formed by a plurality of wires 17 which are spaced circumferentially about the axis of the instrument. The wires extend between the distal end of a sleeve 18 which surrounds the tubular member and the proximal end of an end cap 19. The wires tend to bow in an outward direction, and the basket is moved between opened and closed positions by advancing and retracting the wires relative to an outer sheath 21. When the basket is advanced, the wires extend from the distal end of the sheath and bow out to the open position for capturing a stone. As the basket is retracted, the wires are drawn together and into the sheath, closing the basket and tightening the wires about a captured stone. Nuts 22, 23 are threaded onto the proximal end portions of sleeve 18 and sheath 21 to clamp the sleeve and sheath in fixed positions relative to tubular member 11 and to each other in order to retain the captured stone in the basket. In FIG. 3, the basket is shown in a partially closed position with a stone 24 in the basket.

The outer diameter of end cap 19 is equal to the outer diameter of sheath 21, and the cap includes a rear flange 26 which mates with the distal end portion of the sheath when the basket is fully retracted. The distal end portion of the cap is rounded to form a smooth tip 27 which facilitates insertion of the extractor into the body.

The proximal end portion of tubular member 11 is formed with a hub 28 of enlarged diameter which is threadedly connected to a housing 29 which forms a handle for the extractor.

A relatively stiff shaft or rod 31 extends through the opening or bore in tubular member 11 and is adapted for movement between axially advanced and retracted positions for breaking stones in the basket into smaller pieces for easier removal from the body. In the embodiment illustrated, the distal end of the shaft is formed with a point 32 which serves as a tip for impacting upon the stones. If desired, the end of the shaft can be formed with a different shape, or a separate tip can be employed.

Means is provided for moving the shaft back and forth between the advanced and retracted positions to impact the tip upon the stone with a hammering action. This means includes a spring 33 which drives the shaft toward the advanced position and a pair of relatively rotatable cams 34, 36 which draw the shaft toward the retracted position against the force of the spring, then release it to be driven forward by the spring.

Cam 34 is connected to the proximal end of shaft 31 and is movable between advanced and retracted positions in an axial bore 37 in housing 29. Spring 33 is positioned between the back side of cam 34 and the inner end of the bore and urges the cam in the forward direction toward its advanced position. Cam 36 is mounted in a fixed position toward the outer end of bore 37 is constructed in the form of a plug which is threadedly received in the outer portion of the bore. A portion of the plug extends beyond the bore, and the hub 28 at the proximal end of tubular member 11 is threaded onto this portion of the plug. Cam 34 has a stem 38 which passes through a bore 39 in cam 36, with a chuck 40 at the distal end of the stem in which the proximal end of shaft 31 is received.

Cams 34, 36 have helically inclined axially facing surfaces 41, 42 which are urged into engagement with each other by spring 33 for moving the shaft from the advanced position to the retracted position upon relative rotation of the cams. Radial steps 43, 44 are formed in the cam surfaces, and when the steps on the two surfaces are aligned with each other, cam 34 and the shaft connected thereto move abruptly in the forward direction under the urging of the spring.

A drive motor 46 is mounted in the proximal, portion of housing 29 and connected to cam 34 by a speed reducing transmission or gear train 47 and a slip joint 48. The motor is energized by current from by batteries (not shown) which are also mounted in the handle, with a switch 49 for controlling the application of current to the motor.

Gear train 47 comprises a spur gear 51 mounted on the output shaft of the motor, an idler gear 52 driven by the spur gear, and a ring gear 53 driven by the idler gear. The gear train has an output shaft 54 affixed to the ring gear in axial alignment with the motor shaft and the rest of the instrument.

Slip joint 48 comprises a hollow shaft 56 affixed to the back side of cam 34 into which drive shaft 54 extends. A laterally extending pin 57 affixed to the hollow shaft is received in a longitudinally extending slot 58 in the drive shaft to constrain the two shafts for rotation together while permitting axial movement between the two shafts.

Operation and use of the stone extractor, and therein the method of the invention, are as follows. The extractor is introduced into the body with the basket in its retracted or closed position. The extractor is introduced together with a cystoscope, a urethroscope or another suitable device for observing the distal end portion of the extractor and the stone. When the distal end portion of the instrument passes slightly beyond the stone to be removed, the basket is opened, and the instrument is manipulated to capture the stone in the basket. Once the stone has been captured, the basket is closed about the stone to retain the stone in the basket. Nuts 22, 23 are then tightened to prevent further movement of the basket relative to tubular member 11 and sheath 21.

Once the stone has been captured, drive motor 46 is energized to rotate cam 34 in a counterclockwise direction as viewed from behind. Spring 33 urges the faces 41, 42 of the two cams together, and the rotation of cam 34 brings progressively high portions of the inclined surfaces together, forcing the two cams apart and moving shaft 31 toward its retracted position against the force of the spring. When cam 34 rotates to the point where steps 43, 44 are aligned, i.e. slightly beyond the position shown in FIG. 2, cam 34 moves abruptly toward its advanced position under the force of spring 33, driving tip 32 into the stone in the basket. As the motor continues to rotate, shaft 31 is repeatedly retracted and released, with tip 32 being driven into the stone each time the shaft is released. The impact of the tip on the stone breaks the stone into smaller pieces which can then be withdrawn from the body in the basket. Since the hammering action takes place inside the basket, the stone breaking tip cannot impact upon the tissue surrounding the stone, and the tissue is thus protected from injury by the tip.

Figure 5:
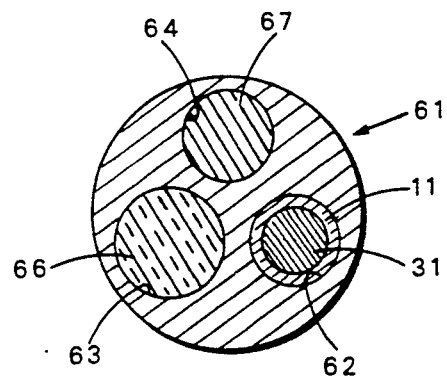
FIG. 5 is a cross-sectional view taken along line 5—5 in FIG. 4.

In the embodiment of FIGS. 4-5, the extractor is combined with an instrument 61 such as a cystoscope or a urethroscope which has three longitudinally extending luminal openings or bores 62-64. Tubular member 11 and shaft 31 extend through bore 62 and function in the same manner as in the embodiment of FIGS. 1-3. An optical system 66 of a type commonly utilized in endoscopes and urethroscopes passes through bore 63 to permit visual observation of the stone as it is captured and broken up. The wires 17 which form basket 16 are twisted together to form a shaft 67 which passes loosely through bore 64 for axial movement to open and close the basket.

Operation and use of the embodiment of FIGS. 4-5 is similar to that of the embodiment of FIGS. 1-3, except that it is not necessary to use a separate cystoscope or other observational device. Also, the basket operating shaft is now offset laterally from the hammer shaft, rather than being disposed coaxially of it. This means that the axis of the hammer is offset slightly from the centerline of the basket so that a stone held by the basket is struck slightly off center. However, this does not present a problem since most stones which will be broken up are substantially larger than the catheter, e.g. ten times the diameter of the catheter. Having the basket separated from the hammer allows the basket to have a solid shaft, and this permits readily available and relatively inexpensive conventional baskets to be used.

Figure 6:
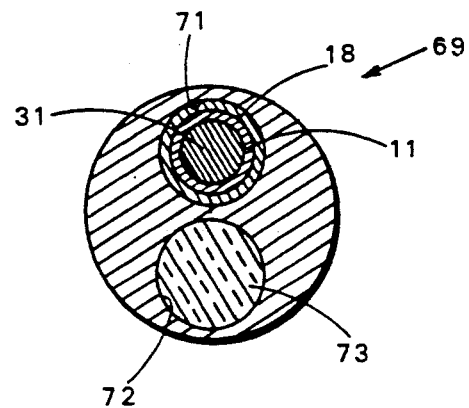
FIG. 6 is view similar to FIG. 5 of another embodiment of a stone extractor incorporating the invention.

The embodiment shown in FIG. 6 includes an instrument 69 such as a cystoscope or urethroscope with two longitudinally extending luminal openings or bores 71-72. Sleeve 18, tubular member 11 and shaft 31 extend through bore 71 and function in the same manner as in the embodiment of FIGS. 1-3. An optical system 73 of a type commonly utilized in endoscopes and urethroscopes passes through bore 72 to permit visual observation of the stone as it is captured and broken up.

Operation and use of the embodiment of FIG. 6 is similar to that of the other embodiments. The extractor is introduced into the body with the cystoscope or urethroscope, and once the basket has been manipulated to capture the stone, the motor is energized to alternately withdraw and release the pointed shaft for impact with the stone.

It is apparent from the foregoing that a new and improved stone extractor and method have been provided. While only certain presently preferred embodiments have been described in detail, as will be apparent to those familiar with the art, certain changes and modifications can be made without departing from the scope of the invention as defined by the following claims.

We claim:

1. In an instrument for removing a stone from the body of a person: an elongated tubular member adapted to be introduced into the body with a distal end portion of the tubular member in proximity to a stone and a proximal end portion of the tubular member outside the body, a shaft extending axially within the tubular member for movement between advanced and retracted positions and having a tip at one end thereof, a spring urging the shaft toward the advanced position to impact the tip upon the stone, a pair of relatively rotatable cam members operatively connected between the tubular member and the shaft and having helically inclined axially facing surfaces in mating engagement with each other for moving the shaft from the advanced position to the retracted position against the urging of the spring, radial steps in the cam surfaces which when aligned with each other permit the shaft to move abruptly from the retracted position to the advanced position under the urging of the spring, and a drive motor connected to one of the cam members for effecting relative rotation of the cam members so that the shaft is alternately moved to the retracted position and released for movement toward the advanced position with the tip impacting upon the stone to break the stone into pieces for removal from the body.

2. The instrument of claim 1 wherein the drive motor is connected to the said one of the cam members by a gear train.

3. In an instrument for removing a stone from the body of a person: an elongated shaft movable between axially advanced and retracted positions and adapted to be introduced into the body with a distal end portion of the shaft in axial alignment with a stone, a tip at the distal end of the shaft for impact with the stone when the shaft is in the advanced position, a spring urging the shaft toward the advanced position, and rotatively driven means for cyclically moving the shaft from the advanced position to the retracted position against the force of the spring and releasing the shaft from the retracted position to permit the spring to drive the shaft toward the advanced position with the tip at the distal end of the shaft impacting upon the stone to break the stone into pieces for removal from the body.

4. The instrument of claim 3 wherein the tip is formed as an integral part of the shaft.

5. In an instrument for removing a stone from the body of a person: an elongated tubular member having proximal and distal ends, a basket at the distal end of the tubular member for capturing and holding a stone, an elongated shaft extending coaxially within the tubular member and into the basket for movement between axially advanced and retracted positions, a stone breaking tip at one end of the shaft for impact with a stone held by the basket when the shaft is in the advanced position, a spring urging the shaft toward the advanced position, and means for cyclically moving the shaft from the advanced position to the retracted position against the force of the spring and releasing the shaft from the retracted position to permit the spring to drive the shaft toward the advanced position with the tip at the distal end of the shaft impacting upon a stone held by the basket to break the stone into pieces for removal form the body.

6. The instrument of claim 5 wherein the stone breaking tip is formed as an integral part of the shaft.

7. The instrument of claim 5 including a sheath surrounding the tubular member and adapted for movement relative to the tubular member for opening and closing the basket.

8. In an instrument for removing a stone from the body of a person: an elongated observational instrument having proximal and distal ends and a plurality of longitudinally extending bores, a basket at the distal end of the observational instrument for capturing and holding a stone, an element for operating the basket extending through one of the bores, means passing through one of the bores for observing the stone, an elongated shaft extending through one of the bores and into the basket, a stone breaking tip at one end of the shaft, a spring urging the shaft toward an advanced position to impact the tip upon a stone held by the basket, and means for cyclically withdrawing the shaft away from the advanced position against the force of the spring and releasing the shaft to permit the spring to drive the shaft toward the advanced position with the tip impacting upon the stone held by the basket to break the stone into pieces for removal from the body.

9. The instrument of claim 8 wherein the element for operating the basket comprises tubular sleeve positioned coaxially about the shaft in one of the bores.

10. In an instrument for removing a stone from the body of a person: an elongated observational instrument having proximal and distal ends and a plurality of longitudinally extending bores, a basket at the distal end of the observational instrument for capturing and holding a stone, an element for operating the basket extending through one of the bores, means passing through one of the bores for observing the stone, an elongated shaft extending through one of the bores and into the basket, a stone breaking tip at the distal end of the shaft, with the shaft and the element for operating the basket being disposed in different ones of the bores, and means at the proximal end of the observational instrument for moving the shaft back and forth between axially advanced and retracted positions to impact the tip upon a stone held by the basket to break the stone into pieces for removal from the body.

11. In an instrument for removing a stone from the body of a person: an elongated observational instrument having proximal and distal ends and a plurality of longitudinally extending bores, a basket at the distal end of the observational instrument for capturing and holding a stone, an element for operating the basket extending through one of the bores, means passing through one of the bores for observing the stone, an elongated shaft extending through one oft he bores and into the basket, a stone breaking tip at the distal end of the shaft, and means at the proximal end of the observational instrument for moving the shaft back and forth between axially advanced and retracted positions to impact the tip upon a stone held by the basket to break the stone into pieces for removal form the body, said means for moving the shaft back and forth comprising a spring urging the shaft toward the advanced position, a pair of relatively rotatable cam members connected to the shaft and having helically inclined axially facing surfaces in mating engagement with each other for moving the shaft from the advanced position to the retracted position against the urging of the spring, radial steps in the cam surfaces which when aligned with each other permit the shaft to move abruptly from the retracted position to the advanced position under the urging of the spring, and a drive motor connected to one of the cam members for effecting relative rotation of the cam members so that the shaft is alternately moved to the retracted position and released for movement toward the advanced position.

12. In a method of removing a stone from the body of a person, the steps of: inserting an elongated shaft into the body with a distal end portion of the shaft in axial alignment with the stone and a tip at the distal end of the shaft in position to impact upon the stone, urging the shaft toward an advanced position with a spring, and cyclically withdrawing the shaft form the advanced position to a retracted position against the urging of the spring and releasing the shaft from the retracted position to permit the spring to drive the shaft toward the advanced position with the tip at the distal end of the shaft impacting upon the stone to break the stone into pieces, and removing said shaft and pieces from the body.

13. In a method of removing a stone from the body of a person, the steps of: inserting an elongated tubular member having proximal and distal ends into the body, capturing a stone in a basket at the distal end of the tubular member, urging an elongated shaft toward an axially advanced position within the tubular member with a drive spring, cyclically withdrawing the shaft away from the advanced position against the force of the spring and releasing the shaft to permit the spring to drive the shaft toward the advanced position to impact the stone in the basket and break the stone into pieces, and withdrawing the tubular member from the body with the pieces of the stone in the basket.

* * * * *